(12) United States Patent
Burkatovsky

(10) Patent No.: US 8,570,523 B2
(45) Date of Patent: *Oct. 29, 2013

(54) METHOD FOR DISCRIMINATING BETWEEN OBJECTS

(75) Inventor: Vitaly Burkatovsky, Rishon le Zion (IL)

(73) Assignee: Eastman Kodak Company, Rochester, NY (US)

( * ) Notice: Subject to any disclaimer, the term of this patent is extended or adjusted under 35 U.S.C. 154(b) by 594 days.

This patent is subject to a terminal disclaimer.

(21) Appl. No.: 12/874,256

(22) Filed: Sep. 2, 2010

(65) Prior Publication Data

US 2012/0057162 A1    Mar. 8, 2012

(51) Int. Cl.
*G01N 21/55* (2006.01)
*G01N 21/86* (2006.01)
*G06K 9/74* (2006.01)
*G01V 8/00* (2006.01)

(52) U.S. Cl.
USPC .......................... 356/448; 356/71; 250/559.4

(58) Field of Classification Search
None
See application file for complete search history.

(56) References Cited

U.S. PATENT DOCUMENTS

| | | | | |
|---|---|---|---|---|
| 3,105,151 A | * | 9/1963 | Nash | 250/559.42 |
| 3,922,090 A | * | 11/1975 | Fain | 356/71 |
| 4,947,441 A | * | 8/1990 | Hara et al. | 382/135 |
| 6,800,868 B2 | | 10/2004 | Kawamura et al. | |
| 6,825,484 B2 | | 11/2004 | Burkatovsky | |
| 7,157,725 B2 | | 1/2007 | Kawamura et al. | |
| 7,397,747 B2 | * | 7/2008 | Kikuchi et al. | 369/53.22 |
| 2003/0207185 A1 | | 11/2003 | Higashi | |
| 2004/0051862 A1 | * | 3/2004 | Alcock et al. | 356/71 |
| 2012/0057166 A1 | * | 3/2012 | Burkatovsky | 356/448 |

FOREIGN PATENT DOCUMENTS

| | | |
|---|---|---|
| CA | 2 438 070 | 3/2004 |
| JP | 02-210291 | 8/1990 |
| JP | 04-197947 | 7/1992 |

\* cited by examiner

*Primary Examiner* — Gordon Stock, Jr.
(74) *Attorney, Agent, or Firm* — Nelson Adrian Blish

(57) ABSTRACT

A method for discrimination between a first (308) and a second surface (304) type based on reflectivity has a light source (416) that illuminates on a media surface. A photosensor (420) receives and measures the reflection value from the surface. A first gain element adjusts a voltage from the photosensor and a second gain element adjusts a current measurement supplied to the light source. A subtractor (530) for subtracting the first adjusted voltage (534) and the adjusted measurement (538) are subtracted to provide an output value close to zero with respect to the second surface and near a maximum with respect to the first surface. The adjusted reflection value and a threshold reference value (428) are compared (124) and indicates whether the first surface or the second surface is present.

4 Claims, 8 Drawing Sheets

METHOD FOR DISCRIMINATING BETWEEN OBJECTS

CROSS REFERENCE TO RELATED APPLICATIONS

Reference is made to commonly-assigned copending U.S. patent application Ser. No. 12/874,249 (now U.S. Pat. No. 8,427,648), filed Sep. 2, 2010, entitled APPARATUS FOR DISCRIMINATING BETWEEN OBJECTS, by Burkatovsky; the disclosure of which is incorporated herein.

FIELD OF THE INVENTION

The present invention relates in general to a method for discriminating between two objects based on surface reflectivity differences, and more specifically to discriminating between printing plates covered by a polymer emulsion and interleaf paper between the plates.

BACKGROUND OF THE INVENTION

A computer-to-plate (CTP) device 204, shown in FIG. 2, is used for direct imaging on printing plates. The plates are loaded in a magazine or cassette and delivered one by one to be exposed by the imaging device. Alternatively the plates can be provided by an automatic plate loader (APL) 104, wherein a plates stack 108 is inserted into the APL as is shown in FIG. 1. The plates 304 provided in the cassette or in a plate stack 104 are usually separated by interleaf paper 308, shown in FIG. 3, interposed between the plates to prevent the emulsion-covered surfaces of the plates from being damaged.

In the course of imaging plates, the plate placed at the top of the stack is picked and transferred to the exposure area for imaging. When an interleaf paper (slip-sheet) is at the top of the stack, the paper is picked and disposed of, before picking the plate. There is a need for discriminating between plate and the interleaf paper are used, to correctly identify the topmost object on the stack.

U.S. Pat. No. 6,825,484 (Burkatovsky) describes a discriminating device based on measurements of the light reflections from the surfaces with different roughness. For example, discrimination between paper and non-covered by emulsion printing plate will be reliable due to substantially different roughness of paper as opposed to a smooth and glossy plate metal surface. But discrimination between paper and emulsion covered plate will often be inaccurate due to the small difference between their roughness properties.

Another method for discriminating the slip sheets and emulsion covered printing plate described in U.S. Pat. No. 7,157,725 (Kawamura). This method is based on the difference between absorbance (reflectance) of a slip sheet and a plate, irradiated by light of 570-740 nm wavelengths.

Reflectance of emulsions and papers produced by different manufacturers may vary substantially. An example of reflections from papers and emulsions of different manufacturers is shown in FIG. 6. X-axis depicts lighting source current or irradiating intensity I and Y-axis depicts the reflection intensity represented by photosensor output voltage Vr. The reflections from paper slip sheet and emulsion covered plate manufactured by the first manufacturer and measured at predetermined height and light source current is shown by lines 604 and 608 respectively. Reflections from paper slip sheet and emulsion manufactured by the second manufacturer and measured at the same height and light source current is shown by lines 612 and 616. The threshold Vth1 for discrimination between paper and emulsion produced by the first manufacturer according to Kawamura et al., should have value greater than emulsion reflection and less than paper reflection values. While irradiation caused by the same light source current the reflections from paper and emulsion produced by the second manufacturer are smaller. This might happen due to different processes applied for emulsion covered printing plates and slip sheet by different manufacturers. In this case the chosen threshold Vth1 will be greater than paper and emulsion reflections and media discriminating will be impossible.

It should be noted that not only manufacturer media variations and differences between the batches of media lead to reflection deviations. Changing parameters such as distance to media, light source, ambient light are also impact on reflections thus making difficult to practical implementation of the method suggested by Kawamura et al.

The purpose of this invention is to improve the paper slip sheet and emulsion covered plate discrimination capability.

SUMMARY OF THE INVENTION

Briefly, according to one aspect of the present invention a method for discrimination between a first and a second surface type based on reflectivity has a light source that illuminates on a media surface. A photosensor receives and measures the reflection value from the surface. A first gain element adjusts a voltage from the photosensor and a second gain element adjusts a current measurement supplied to the light source. A subtractor for subtracting the first adjusted voltage and the adjusted measurement are subtracted to provide an output value close to zero with respect to the second surface and near a maximum with respect to the first surface. The adjusted reflection value and a threshold reference value are compared and indicates whether the first surface or the second surface is present.

The invention and its objects and advantages will become more apparent in the detailed description of the preferred embodiment presented below.

DETAILED DESCRIPTION OF THE INVENTION

In the following detailed description, numerous specific details are set forth in order to provide a thorough understanding of the disclosure. However, it will be understood by those skilled in the art that the teachings of the present disclosure may be practiced without these specific details. In other instances, well-known methods, procedures, components and circuits have not been described in detail so as not to obscure the teachings of the present disclosure.

While the present invention is described in connection with one of the embodiments, it will be understood that it is not intended to limit the invention to this embodiment. On the contrary, it is intended to cover all alternatives, modifications, and equivalents as covered by the appended claims.

Figure 1:
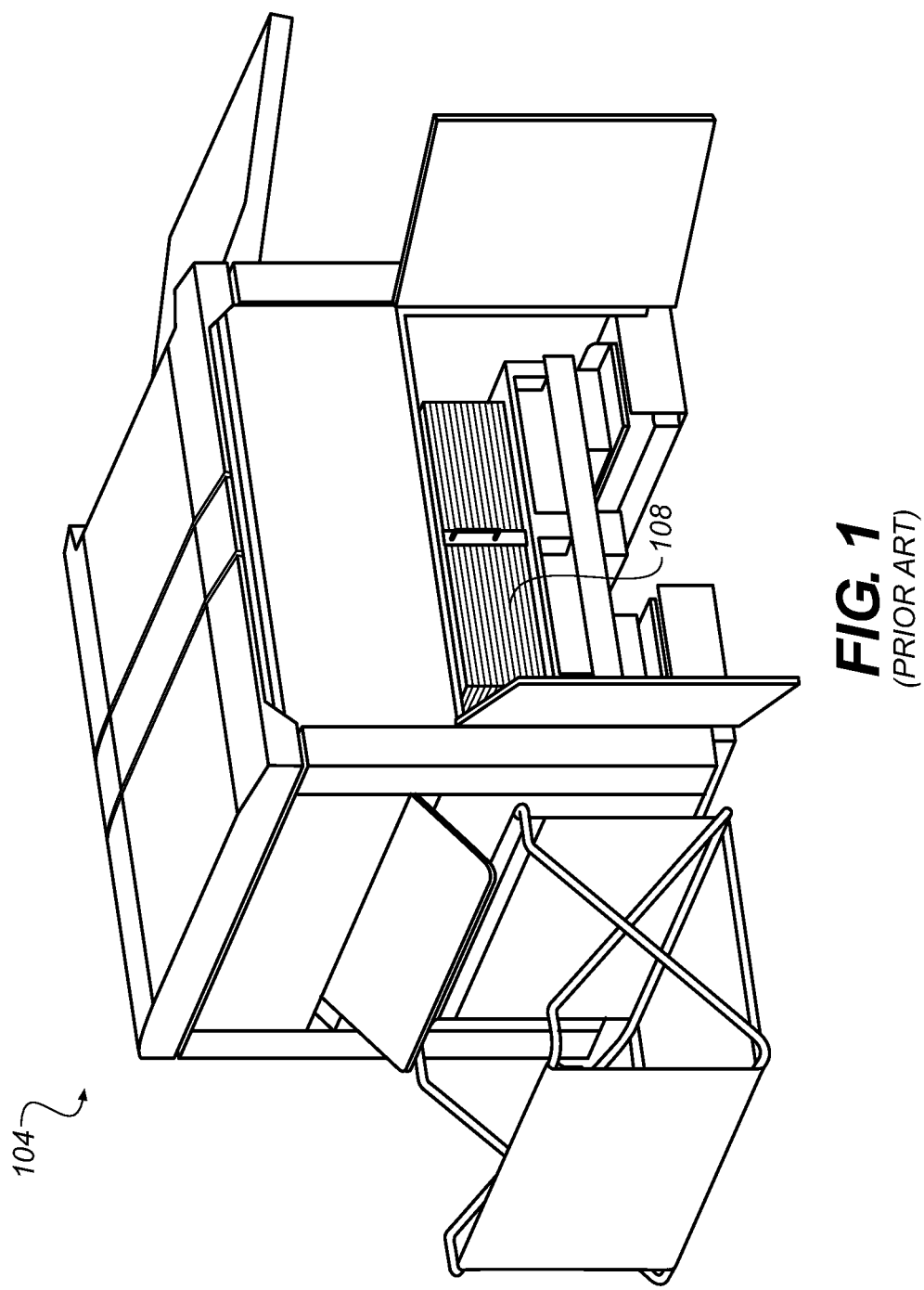
FIG. 1 is a schematic illustration of an automatic plate loader (APL) loaded with stack of plates (prior art)
Figure 2:
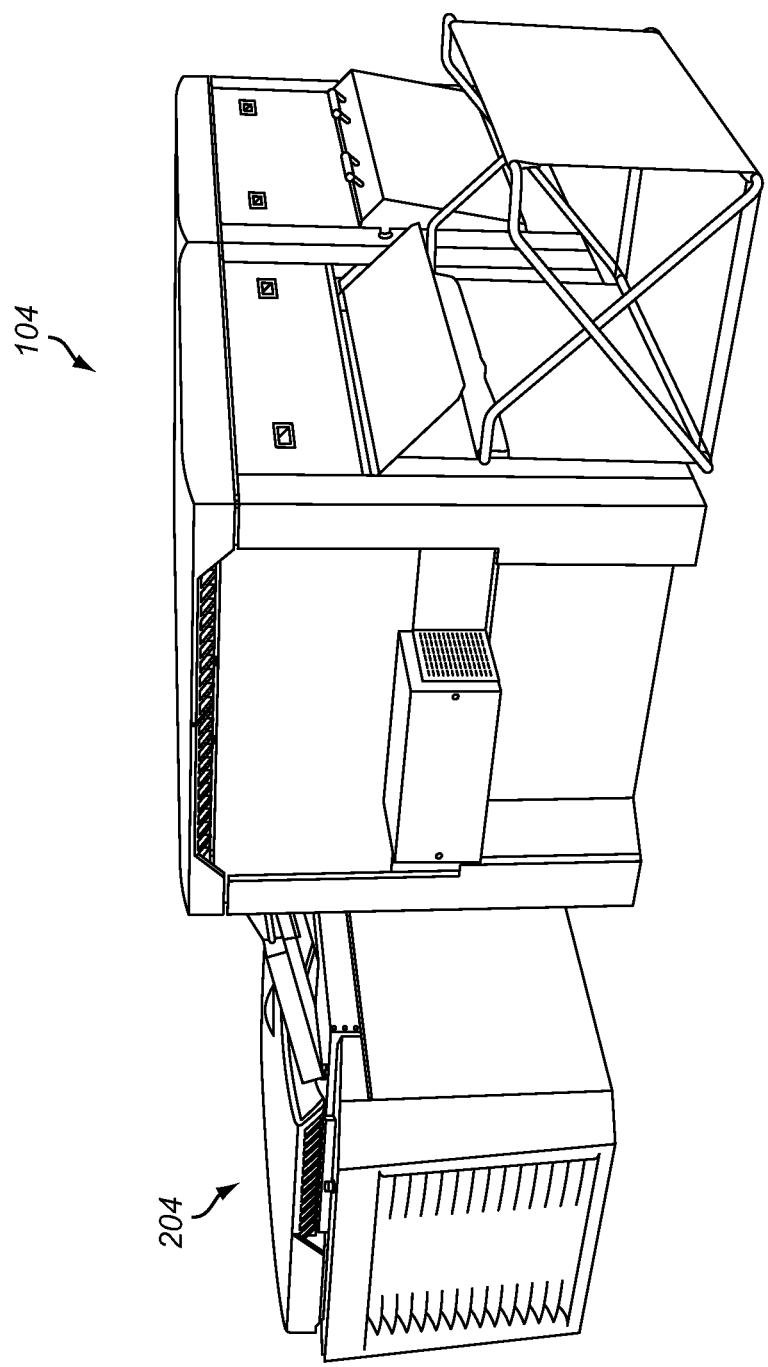
FIG. 2 shows an imaging device connected to an APL (prior art)
Figure 3:
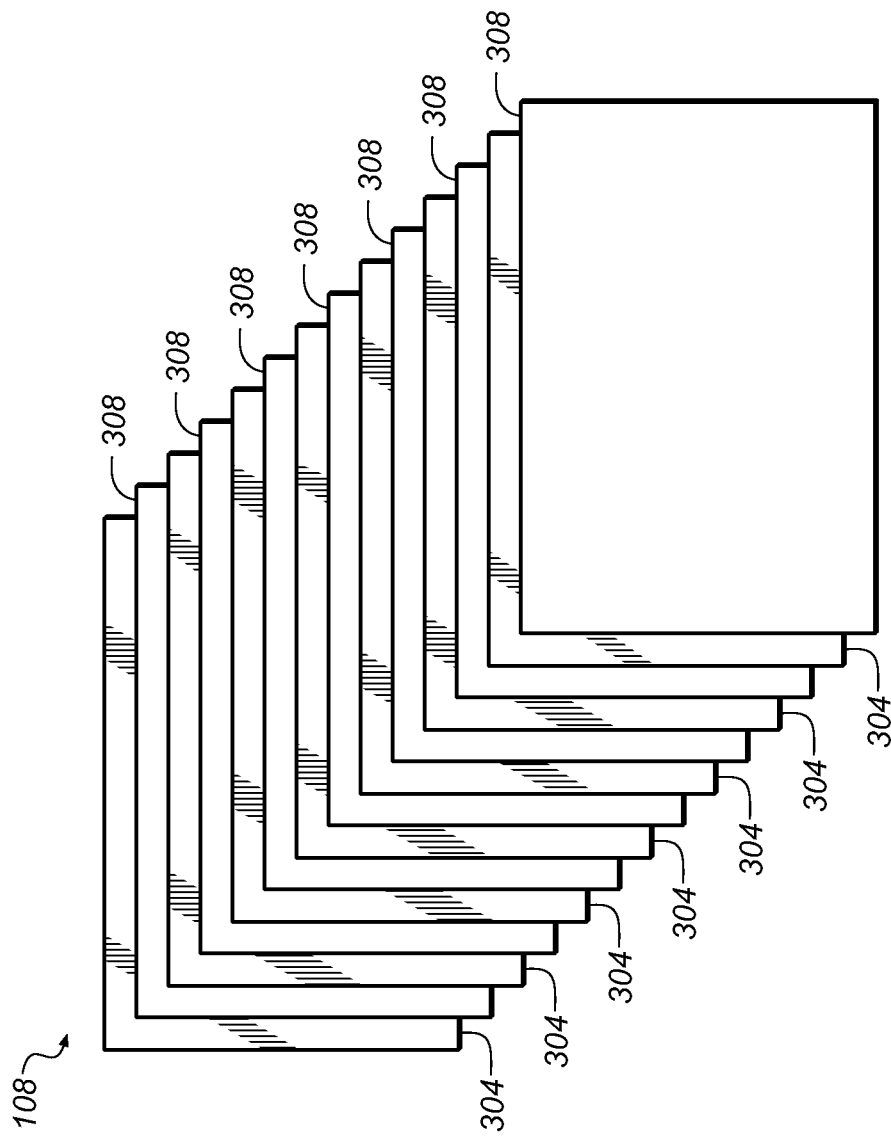
FIG. 3 is a schematic illustration of a plates stack, showing plates separated by slip sheets (prior art)
Figure 4:
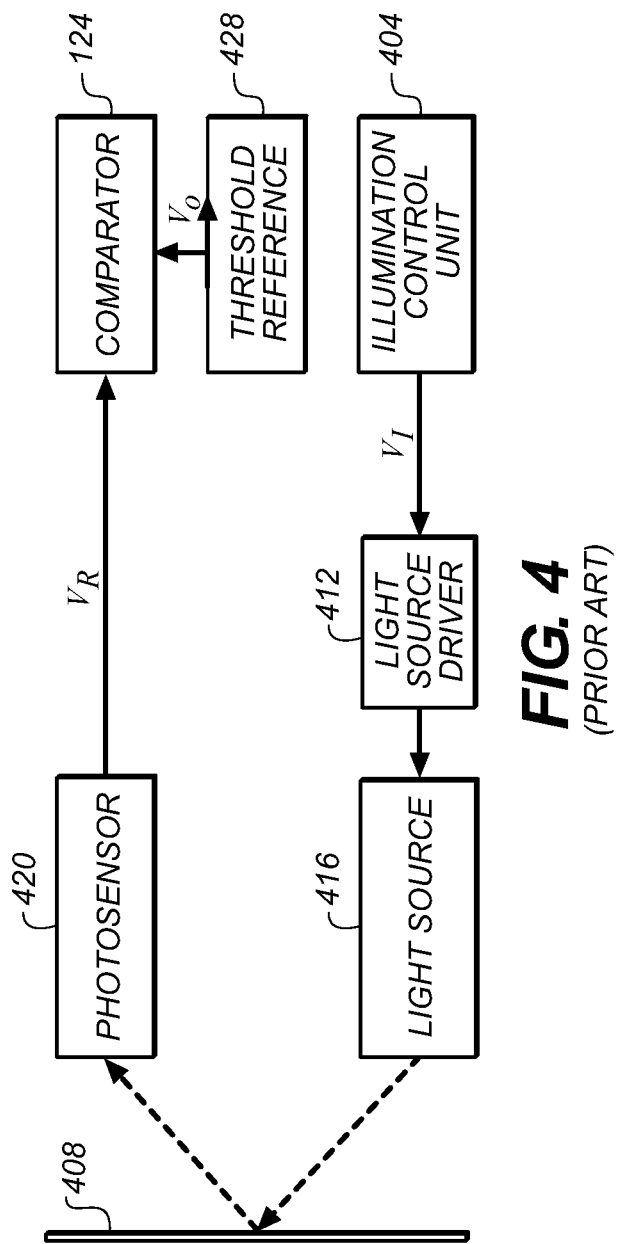
FIG. 4 is a schematic illustration of paper/plate discrimination device known in the art.
Figure 5:
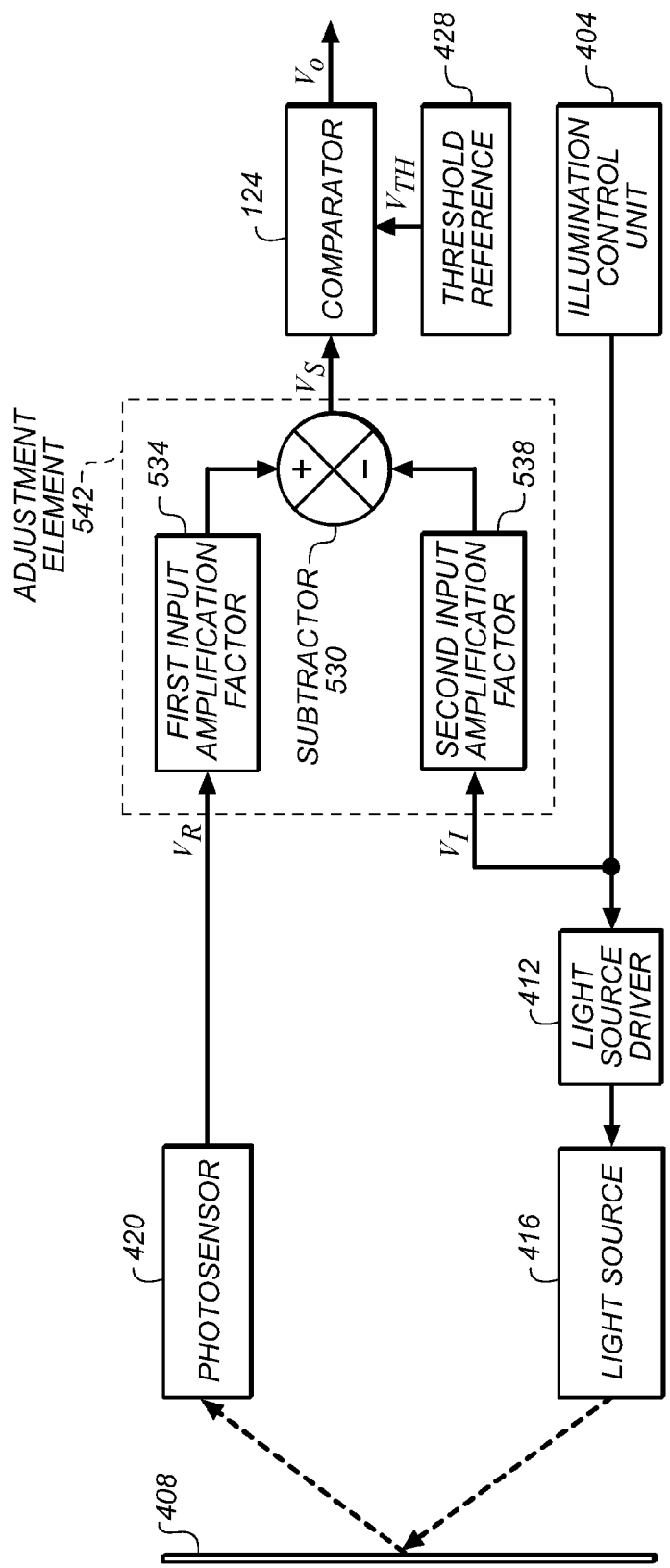
FIG. 5 is a schematic illustration of the discrimination device proposed by the current disclosure.

The schematic illustration of a discriminating device known the art is shown in FIG. 4. FIG. 5 shows components of the proposed invention, where some of the components are also being used in the Kawamura et al., as are shown in FIG. 4. The illumination control unit 404 intended for setting the level of media 408 illumination connected through the light source driver 412 to the light source 416, the light source can be a LED (light emitting diode). The reflections from media 408 are measured by photosensor 420.

An adjustment element 542 is connected by its inputs to the outputs of the photosensor 420 and the illumination control unit 404. The output of the adjustment element 542 is connected to the first input of comparator 124 while the second input of comparator 124 is connected to the threshold reference 428.

The irradiation of the tested media provided by the light source 416 controlled by the illumination set point signal Vi produced by illumination control unit 404 through the light source driver 412. The photosensor 420 generates signal $V_R$ proportional to the reflection from tested media. This signal is amplified by first input amplification factor 534 ($G_R$) of adjustment element 542, simultaneously the illumination set point signal Vi is gained (divided) by second input amplification factor 538 (Gi) and than subtracted by subtractor 530 from the gained $V_R$ signal. The result of the subtraction is represented by subtractor output value signal $V_S$ complying with following equation:

$$V_S = V_R * G_R - V_i * G_i \quad (1)$$

Figure 7:
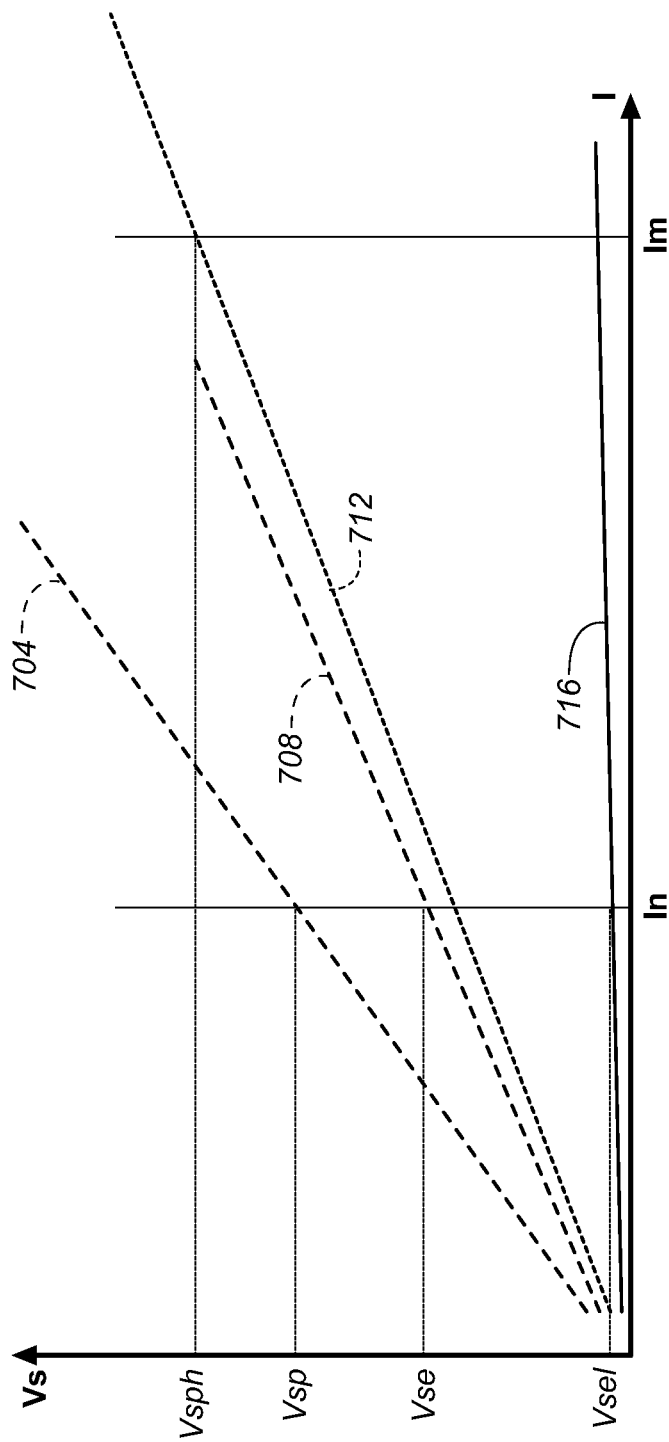
FIG. 7 is shows a graph of amplification factors selection.

FIG. 7 explains the selection of $G_R$ and Gi which is substantial for suggested discriminating device. Assuming $G_{R0}=1$ and $Gi_0=0$.

In this case according to Equation (1) VS will equal to VR.

$$V_S = V_R \quad (2)$$

In the case when VS equals VR, according to Equation (1), the behavior of the proposed discrimination device shown in FIG. 5 will behave as the device described by Kawamura et al, which is shown in FIG. 4.

Figure 6:
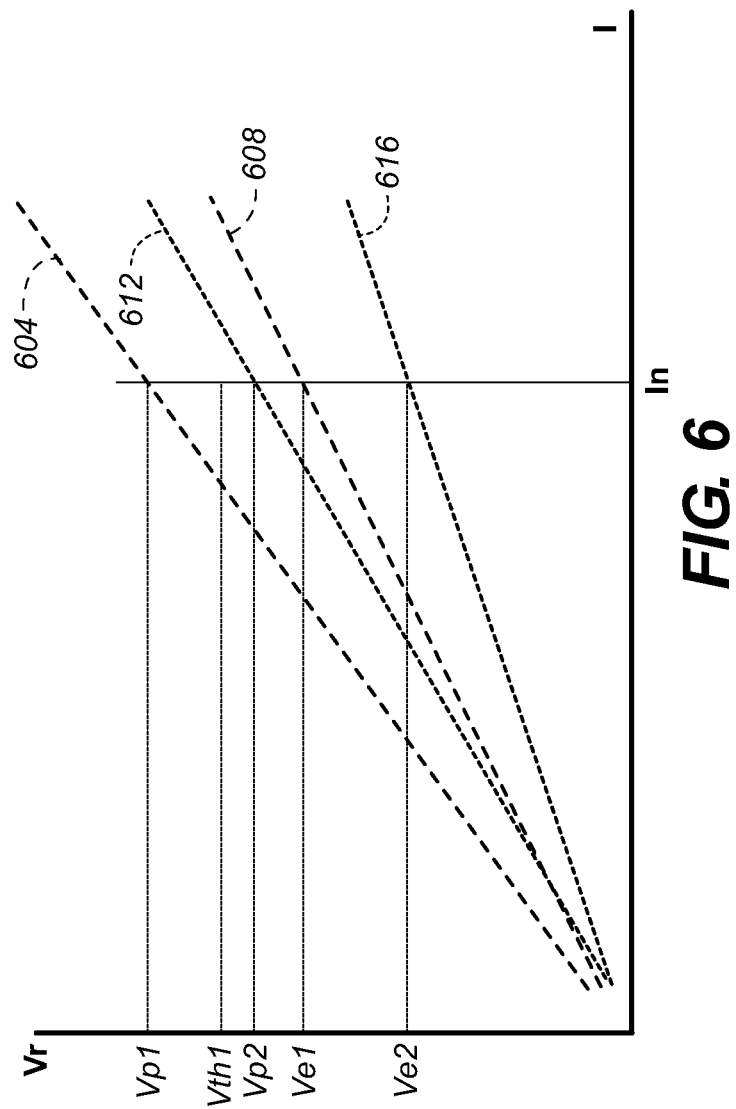
FIG. 6 is shows a behavior function of reflection from various media objects.

Line 704 in FIG. 7 shows a response function representing the reflection from paper slip sheet and line 708 represents reflection from emulsion covered plate surface respectively. These lines are identical to lines 604 and 608 of FIG. 6. Respectively Vsp=Vpl and Vse=Vel. The relation between the Vsp and Vse determines the capability of the device to perform a reliable discrimination between paper slip sheets and emulsion covered plates. The relation between amplified paper reflection and amplified (divided) emulsion reflection is defined as discrimination factor DF.

$$DF = Vsp/Vse \quad (3)$$

As much as the Vsp value is bigger than Vse value, the discrimination will be more reliable, due to covering of a larger reflection range and thus decreasing the sensitivity of reflection deviations.

In other words in order to improve the discrimination capability of a discrimination device the value of DF needs to be increased. This can be achieved by adjusting the amplification factors 534 ($G_R$) and 538 (Gi). The Gi adjustment should be provided while emulsion covered printing plate is examined.

Adjustment may start with mentioned above values of $Gi_0$ and $G_{R0}$. ($Gi_O=0$, $G_{RO}=1$). According to equations (2) and (3) discrimination factor for these values will be defined as $$DF_0 = Vsp_0/Vse_0. \quad (4)$$

Now by increasing 538 (Gi) up to the moment when Vse will be close to zero we obtain the situation when Vse is practically not dependent upon the light source 416 current and remains low within the light source current possible range (line 716). Respectively after adjusting 538 (Gi) while examining the paper slip sheet, the Vsp line 704 will change its slope. The Vsp dependence on light source 416 current after Gi adjustment is presented by line 712.

Increasing the light source 416 current to Im by means of illumination control unit 404 we obtain Vsph value while examining paper and Vsel value while examining emulsion covered plate. As Vsph is bigger than Vsp and Vsel is lower than Vse thus according to equation (3) the value of representing discrimination factor $$DF1 = Vsph/Vsel \quad (5)$$

will be much bigger than $DF_0$ (4), thus yielding a substantially improved discrimination capabilities. The maximum value of Vsph is restricted by power supply voltage. In other words the threshold margin is enough to support the discrimination of plates and emulsions from various manufacturers.

It should be noted that the DF1 value may be achieved also without light source 416 current changing (from In to Im). This can be obtained by increasing the amplification factor 534 ($G_R$) while maintaining line 716 close to the X-Axis (as is shown in FIG. 7), by adjusting the amplification factor 538 (Gi).

Figure 8:
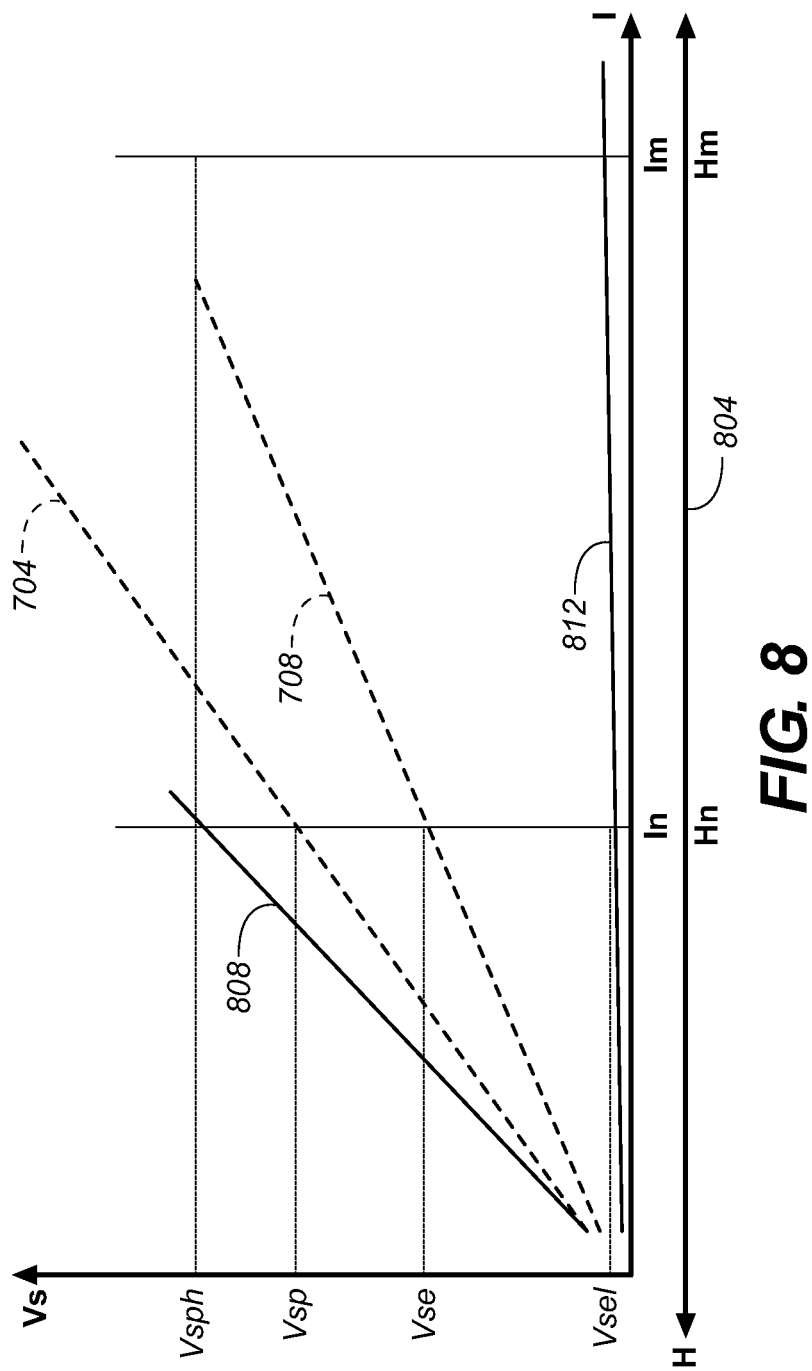
FIG. 8 is shows the discrimination behavior of the suggested device in response to the distance from the measured target.

FIG. 8 depicts the subtractor output value $V_S$ signal used in FIG. 7 as a function of media to sensor distance shown as axis H (804). Comparing to FIG. 7 point Hn of axis H determines the media to sensor distance while illuminating current value is In. Reflections from paper slip sheet and emulsion covered plate at this point are the same as shown on FIG. 6 (Vpl and Vel). Respectively the subtractor output values while $Gi_O=0$ and $G_{RO}=1$ are Vsp and Vse, the same as shown on FIG. 7. Now while maintaining the constant value of LED current. In the amplification factors 534 ($G_{RO}$) and 538 ($Gi_O$) should be adjusted such as subtractor output value $V_S$ is close to zero Vsel in response to lower reflectance surface type (emulsion covered plate). As a result of the subtractor output value $V_S$ is maximal Vsph in response to higher reflectance surface type (slip slit paper). The subtractor output value behavior represents the emulsion covered plate reflection after gains adjustment is depicted by line 812. Respectively the subtractor output value behavior for the slip sheet paper reflection after gains adjustment is represented by behavior function 808 (sensor to media distance is bigger than Hn) and line Vsph—maximum voltage value restricted by power supply voltage (sensor to media distance is smaller than Hn).

As it can be seen from FIG. 8 the range from smaller media to sensor distance Hm to higher media to sensor distance Hn shows practically same subtractor output values such as Vsel close to zero in the case of emulsion testing and Vsph close to power supply voltage in case of slip sheet paper testing. Within this (Hm–Hn) range the discrimination factor has maximum allowable value DF=(Vsph/Vsel) according to Equation (3) and DF=constant as well. Referring to the prior art performance according to FIG. 8, in the Hn sensor to media distance point the prior art device will have a worse DF than the suggested device as is shown by Equations (4) and (5). In addition the Hm sensor to media distance point in prior art device will not work at all, due to very high incoming reflection. Specific gains adjustment allows discrimination performance practically independent of sensor to media distance and extending of sensor to media distance range where discriminating is possible.

The invention has been described in detail with particular reference to certain preferred embodiments thereof, but it will be understood that variations and modifications can be effected within the scope of the invention.

PARTS LIST

| | |
|---|---|
| 104 | automatic plate loader |
| 108 | plate stack |
| 124 | comparator |
| 204 | computer-to-plate (CTP) device |
| 304 | plates (with emulsion surface up) |
| 308 | interleaf paper (slip sheets) |
| 404 | illumination control unit |
| 408 | media |
| 412 | light source driver |
| 416 | light source |
| 420 | photosensor |
| 428 | threshold reference |
| 530 | subtractor |
| 534 | first input amplification factor |
| 538 | second input amplification factor |
| 542 | adjustment element |
| 604 | sheet slip reflection graph a first plate manufacturer |
| 608 | emulsion surface reflection graph a first plate manufacturer |
| 612 | sheet slip reflection graph from a second plate manufacturer |
| 616 | emulsion surface reflection graph a second plate manufacturer |
| 704 | slip sheet reflection graph a first plate manufacturer |
| 708 | emulsion surface reflection graph a first plate manufacturer |
| 712 | adjusted slip sheet reflection graph |
| 716 | adjusted emulsion surface reflection graph |
| 804 | height axis |

-continued

PARTS LIST

| | |
|---|---|
| 808 | slip sheet reflection behavior function after gains |
| 812 | emulsion surface reflection behavior function after gains |

The invention claimed is:

1. A method for discriminating between a first surface type and a second surface type wherein said first surface type's reflectivity is greater than said second surface type's reflectivity comprising:

illuminating said first or said second surface type with a light source;

measuring a reflectivity of said first surface type or said second surface type;

adjusting a voltage gain or current gain based on said measured reflectivity to provide a first adjusted voltage or current;

adjusting a measurement of a current or a voltage supplied to said light source;

subtracting the first adjusted voltage or current from the adjusted measurement to provide a subtractor output value;

providing a threshold reference value; and comparing said subtractor output value with said threshold reference value to determine whether said first surface type or said second surface type is present.

2. The method according to claim 1 wherein said light source is a LED.

3. The method according to claim 1 wherein said second surface type is an emulsion covered surface.

4. The method according to claim 1 wherein said first surface type is a slip sheet paper.

* * * * *